United States Patent
Chreng

(10) Patent No.: US 9,758,546 B2
(45) Date of Patent: Sep. 12, 2017

(54) METHOD FOR SOLUTION PHASE DETRITYLATION OF OLIGOMERIC COMPOUNDS

(71) Applicant: Ionis Pharmaceuticals, Inc., Carlsbad, CA (US)

(72) Inventor: Dana Chreng, San Marcos, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/027,505

(22) PCT Filed: Oct. 21, 2014

(86) PCT No.: PCT/US2014/061454
§ 371 (c)(1),
(2) Date: Apr. 6, 2016

(87) PCT Pub. No.: WO2015/061246
PCT Pub. Date: Apr. 30, 2015

(65) Prior Publication Data
US 2016/0244477 A1 Aug. 25, 2016

Related U.S. Application Data

(60) Provisional application No. 61/893,569, filed on Oct. 21, 2013, provisional application No. 61/952,678, filed on Mar. 13, 2014.

(51) Int. Cl.
| | | |
|---|---|---|
| C07H 21/00 | (2006.01) | |
| C07H 21/04 | (2006.01) | |
| C07H 1/00 | (2006.01) | |
| C07H 1/06 | (2006.01) | |

(52) U.S. Cl.
CPC .............. *C07H 21/04* (2013.01); *C07H 1/00* (2013.01); *C07H 21/00* (2013.01); *C07H 1/06* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,973,679 A | 11/1990 | Caruthers et al. |
| 4,981,957 A | 1/1991 | Lebleu et al. |
| 5,023,243 A | 6/1991 | Tullis |
| 5,034,506 A | 7/1991 | Summerton et al. |
| 5,118,800 A | 6/1992 | Smith et al. |
| 5,132,418 A | 7/1992 | Caruthers et al. |
| RE34,069 E | 9/1992 | Koster et al. |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |

(Continued)

FOREIGN PATENT DOCUMENTS

| | | |
|---|---|---|
| WO | WO 96/03417 | 2/1996 |
| WO | WO 98/47910 | 10/1998 |

(Continued)

OTHER PUBLICATIONS

Altmann et al., "Second-generation antisense oligonucleotides: structure—activity relationships and the design of improved signal-transduction inhibitors" Biochem. Soc. Trans. (1996) 24:630-637.
Altmann et al., "Second Generation of Antisense Oligonucleotides: From Nuclease Resistance to Biological Efficacy in Animals " Chimia. (1996) 50(4):168-176.
Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.
Beaucage et al., "Deoxynucleoside Phosphoramidites—A New Class of Key Intermediates for Deoxypolynucleotide Synthesis" Tetrahedron Letters (1981) 22(20):1859-1862.

(Continued)

*Primary Examiner* — Patrick Lewis
(74) *Attorney, Agent, or Firm* — Ionis Pharmaceuticls, Inc. Patent Dept.

(57) ABSTRACT

Provided herein are methods for the synthesis of oligomeric compounds wherein removal of the 5'-terminal trityl group is performed at reduced temperature and lower pH relative to standard methods. In certain embodiments, the present methods provide detritylated oligomeric compounds having a reduced percentage of depurination relative to the same detritylated oligomeric compounds prepared using standard methods. In certain embodiments, the present methods provide detritylated oligomeric compounds with increased purity relative to the same detritylated oligomeric compounds prepared using standard methods. In certain embodiments, the present method provide an increased rate of detritylation compared to standard methods.

25 Claims, No Drawings

(56) References Cited

U.S. PATENT DOCUMENTS

| | | | |
|---|---|---|---|
| 5,359,044 A | 10/1994 | Cook et al. | |
| 5,366,878 A | 11/1994 | Pederson et al. | |
| 5,399,676 A | 3/1995 | Froehler | |
| 5,405,938 A | 4/1995 | Summerton et al. | |
| 5,405,939 A | 4/1995 | Suhadolnik et al. | |
| 5,434,257 A | 7/1995 | Matteucci | |
| 5,446,137 A | 8/1995 | Maag et al. | |
| 5,453,496 A | 9/1995 | Caruthers et al. | |
| 5,455,233 A | 10/1995 | Spielvogel et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,476,925 A | 12/1995 | Letsinger et al. | |
| 5,489,677 A | 2/1996 | Sanghvi et al. | |
| 5,514,785 A | 5/1996 | Van Ness et al. | |
| 5,519,126 A | 5/1996 | Hecht | |
| 5,519,134 A | 5/1996 | Acevedo et al. | |
| 5,527,899 A | 6/1996 | Froehler | |
| 5,536,821 A | 7/1996 | Agrawal et al. | |
| 5,541,306 A | 7/1996 | Agrawal et al. | |
| 5,541,307 A | 7/1996 | Cook et al. | |
| 5,550,111 A | 8/1996 | Suhadolnik et al. | |
| 5,561,225 A | 10/1996 | Maddry et al. | |
| 5,563,253 A | 10/1996 | Agrawal et al. | |
| 5,565,555 A | 10/1996 | Froehler et al. | |
| 5,567,811 A | 10/1996 | Mistura et al. | |
| 5,571,799 A | 11/1996 | Tkachuk et al. | |
| 5,576,427 A | 11/1996 | Cook et al. | |
| 5,587,361 A | 12/1996 | Cook et al. | |
| 5,591,722 A | 1/1997 | Montgomery et al. | |
| 5,596,086 A | 1/1997 | Matteucci | |
| 5,597,909 A | 1/1997 | Urdea et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,618,704 A | 4/1997 | Sanghvi et al. | |
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,646,265 A | 7/1997 | McGee | |
| 5,646,269 A | 7/1997 | Matteucci | |
| 5,663,312 A | 9/1997 | Chaturvedula | |
| 5,670,633 A | 9/1997 | Cook et al. | |
| 5,672,697 A | 9/1997 | Buhr et al. | |
| 5,677,437 A | 10/1997 | Teng et al. | |
| 5,677,439 A | 10/1997 | Weis et al. | |
| 5,700,920 A | 12/1997 | Altmann et al. | |
| 5,721,218 A | 2/1998 | Froehler | |
| 5,792,608 A | 8/1998 | Swaminathan et al. | |
| 5,792,847 A | 8/1998 | Buhr et al. | |
| 5,808,042 A | 9/1998 | Iyer et al. | |
| 6,268,490 B1 | 7/2001 | Imanishi et al. | |
| 6,399,765 B1 * | 6/2002 | Krotz .................. | C07H 21/00 536/25.31 |
| 6,525,191 B1 | 2/2003 | Ramasamy | |
| 6,600,032 B1 | 7/2003 | Manoharan et al. | |
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 6,867,294 B1 | 3/2005 | Sanghvi et al. | |
| 7,034,133 B2 | 4/2006 | Wengel et al. | |
| 7,053,207 B2 | 5/2006 | Wengel | |
| 7,399,845 B2 | 7/2008 | Seth et al. | |
| 7,547,684 B2 | 6/2009 | Seth et al. | |
| 7,696,345 B2 | 4/2010 | Allerson et al. | |
| 7,741,457 B2 | 6/2010 | Seth et al. | |
| 8,299,206 B2 | 10/2012 | Fox et al. | |
| 2005/0130923 A1 | 6/2005 | Bhat et al. | |
| 2008/0039618 A1 | 2/2008 | Allerson et al. | |
| 2008/0058511 A1 | 3/2008 | Hargreaves et al. | |

FOREIGN PATENT DOCUMENTS

| | | |
|---|---|---|
| WO | WO 99/14226 | 3/1999 |
| WO | WO 2004/106356 | 12/2004 |
| WO | WO 2005/021570 | 3/2005 |
| WO | WO 2005/121371 | 12/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 2/2011 |

OTHER PUBLICATIONS

Beaucage et al., "Advances in the Synthesis of Oligonucleotides by the Phosphoramidite Approach" Tetrahedron (1992) 48(12):2223-2311.

Beaucage et al., "The Functionalization of Oligonucleotides Via Phosphoramidite Derivatives" Tetrahedron (1993) 49(10):1925-1963.

Beaucage et al., "The Synthesis of Specific Ribonucleotides and Unrelated Phosphorylated Biomolecules by the Phosphoramidite Method" Tetrahedron (1993) 49(46):10441-10488.

Braasch et al., "Locked nucleic acid (LNA): fine-tuning the recognition of DNA and RNA" Chem. Biol. (2001) 8:1-7.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Elayadi et al., "Application of PNA and LNA oligomers to chemotherapy" Curr. Opinion Invens. Drugs (2001) 2:558-561.

Frieden et al., "Expanding the design horizon of antisense oligonucleotides with alpha-L-LNA" Nucleic Acids Research (2003) 31(21):6365-6372.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Leumann et al., "DNA Analogues: From Supramolecular Principles to Biological Properties" Bioorganic & Medicinal Chemistry (2002) 10:841-854.

Martin, "Ein neuer Zugang zu 2'-O-Alkylribonucleosiden and Eigenschaften deren Oligonucleotide" Helv. Chim. Acta. (1995) 78(2):486-504.

Orum et al., "Locked nucleic acids: A promising molecular family for gene-function analysis and antisense drug development" Curr. Opinion Mot Ther. (2001) 3:239-243.

Salon et al., "Mild Detritylation of Nucleic Acid Hydroxyl Groups by Warming-Up" Nucleosides, Nucleotides and Nucleic Acids, (2011) 30: 271-279.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines. Synthesis, Structure, and Biochemical Studies" J. Am Chem. Soc. (2007) 129(26):8362-8379.

Wahlestedt et al., "Potent and nontoxic antisense oligonucleotide containing locked nucleic acids" Proc. Natl. Acad. Sci. USA (2000) 97: 5633-5638.

International Search Report PCT/US2014/061454 Oct. 21, 2014 Isis Pharmaceuticals, Inc.

\* cited by examiner

METHOD FOR SOLUTION PHASE DETRITYLATION OF OLIGOMERIC COMPOUNDS

SEQUENCE LISTING

The present application is being filed along with a Sequence Listing in electronic format. The Sequence Listing is provided as a file entitled DVCM0038USASEQ_ST25.txt, created Apr. 5, 2016, which is 8 Kb in size. The information in the electronic format of the sequence listing is incorporated herein by reference in its entirety.

FIELD OF THE INVENTION

The present disclosure is directed to the field of oligomer synthesis. In particular, improvements in the synthesis of oligomeric compounds are provided by modification of the final detritylation step. In certain embodiments, the final detritylation step is performed in solution at reduced temperature and at a lowered pH relative to standard methods. In certain embodiments, modification of the final detritylation step results in less depurination. In certain embodiments, the modification of the final detritylation step results in an improved yield. In certain embodiments, the modification of the final detritylation step results in a faster detritylation of the oligomeric compound compared to standard methods.

BACKGROUND OF THE INVENTION

Oligonucleotides have been used in various biological and biochemical applications. Oligonucleotides have been used as primers and probes for the polymerase chain reaction (PCR), as antisense agents used in target validation, drug discovery and development, as ribozymes, as aptamers, and as general stimulators of the immune system. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients. More recently, Kynamro® (Mipomersen sodium injectable; developed by Isis Pharmaceuticals Inc., Carlsbad, Calif.) has achieved marketing clearance (2013) from the U.S. Food and Drug Administration (FDA), and is currently a treatment of homozygous familial hypercholesterolemia (HoFH). The widespread use of oligonucleotides has led to an increasing demand for rapid, inexpensive and efficient methods for their synthesis.

Synthesis of oligonucleotides is generally performed on solid support by the repeated coupling of phosphoramidite monomers until the predetermined length and sequence is achieved. The resulting full length oligonucleotide is then cleaved from the solid support and purified with a 5'-hydroxyl protecting group left on. The industry standard 5'-hydroxyl protecting group is the 4,4'-dimethoxytrityl (DMT) group. The phosphoramidite method is well known in the art (see for example: Beaucage and Caruthers (1981) Tetrahedron Letters 22:1859-1862; McBride and Caruthers (1983) Tetrahedron Letters 24:245-248; Sinha et al. (1984) Nucleic Acids Res. 12:4539-4557 and Beaucage and Iyer (1992) Tetrahedron 48:2223-2311, each of which is incorporated herein by reference in its entirety).

Large scale synthesis of oligomeric compounds using the phosphoramidite approach is generally performed using solid phase chemistries wherein oligomeric compounds are assembled in an iterative process on a solid support. A first monomer subunit is coupled to a free hydroxyl group attached to a solid support via a series of chemical reactions. This series of chemical reactions is repeated in an iterative manner for each additional monomer subunit until an oligomeric compound having a predetermined length and base sequence is synthesized. After the oligomeric compound has been cleaved from the solid support the DMT-on oligomeric compound is purified by reverse phase liquid chromatography. When the 5'-terminal protecting group is a 4,4'-dimethoxytrityl (DMT) group the oligomeric compound is referred to as a DMT-on oligomeric compound. The trityl group is normally left to simplify the purification step. In certain embodiments, the trityl group is removed before the cleavage of the oligomeric compound from the solid support.

Treatment of the DMT-on oligomeric compound with an acidified aqueous solution removes the 5'-trityl group. Neutralization of the acid quenches the reaction and the resulting detritylated oligomeric compound is precipitated using ethanol. One unwanted side reaction that occurs during this detritylation step is depurination. It has been observed experimentally that when standard methods are used (22° C., pH 3.5, 50 mg/g oligonucleotide concentration, see also examples 1 and 2), the rate of detritylation depends on the 5'-terminal bases especially the terminal base (A>G>T>C; see Example 3), and as the rate of detritylation decreases the percent of depurination increases. Oligomeric compounds having a C or a T at the 5'-end and several 2'-deoxy purine nucleosides have been shown to have longer detritylation times with the detritylated product having higher percentage of depurination. Consequently, there remains a long-felt need for improved methods for performing the final detritylation step that minimize depurination.

Detritylation under warm conditions with mildly acidic buffers to try to limit depurination has been reported (see Salon et al., *Nucleosides, Nucleotides and Nucleic Acids*, 2011, 30, 271-279).

SUMMARY OF THE INVENTION

Provided herein are methods of preparing oligomeric compounds wherein the standard detritylation step for removing the final 5'-trityl group is modified. Specifically, the final detritylation step is performed at reduced temperature and a lower pH relative to standard methods.

In certain embodiments, methods of detritylating 5'-trityl protected oligomeric compounds are provided comprising:

providing an aqueous solution of 5'-trityl protected oligomeric compounds;

cooling the aqueous solution to from about 5° C. to about 15° C.;

adjusting the pH of the cooled aqueous solution to from about 2.0 to about 3.5 by addition of an acid with mixing;

mixing the acidified solution while maintaining the pH from about 2.0 to about 3.5 and maintaining the temperature to from about 5° C. to about 15° C. until essentially all of the 5'-trityl groups are removed; and adjusting the pH of the acidified solution to from about 5.0 to about 7.0 by addition of aqueous sodium hydroxide that is from about 1N to about 10N while maintaining the temperature below about 35° C. to provide the detritylated oligomeric compound.

In certain embodiments, each 5'-trityl group is 4,4'-dimethoxytrityl.

In certain embodiments, the aqueous solution comprises from about 25 to about 150 mg of 5'-trityl protected oligomeric compounds per gram of water.

In certain embodiments, the water used in any of the aqueous solutions is purified. In certain embodiments, the aqueous solution is cooled to from about 7° C. to about 13° C. until essentially all of the 5'-trityl groups are removed. In certain embodiments, the aqueous solution is cooled to about 10° C. until essentially all of the 5'-trityl groups are removed. In certain embodiments, the temperature of the aqueous solution is maintained at about 10° C. during the addition of aqueous sodium hydroxide. In certain embodiments, the temperature of the aqueous solution is maintained below 25° C. during the addition of aqueous sodium hydroxide. In certain embodiments, the pH of the cooled aqueous solution is adjusted to from about 2.0 to about 3.0. In certain embodiments, the pH of the cooled aqueous solution is adjusted to about 2.5.

In certain embodiments, the acid is a weak acid. In certain embodiments, the weak acid is selected from glacial acetic acid, formic acid, citric acid, tartaric acid, malic acid, fumaric acid, lactic acid, ascorbic acid, benzoic acid oxalic acid and salicylic acid. In certain embodiments, the weak acid is a diluted strong acid selected from phosphoric acid, sulfuric acid and hydrochloric acid. In certain embodiments, the weak acid is an alkylated derivative of a strong acid selected from methanesulfonic acid, monochloroacetic acid, dichloroacetic acid and trifluoroacetic acid. In certain embodiments, the weak acid is glacial acetic acid. In certain embodiments, the weak acid is formic acid.

In certain embodiments, the concentration of the aqueous sodium hydroxide is from about 7N to about 10N. In certain embodiments, the concentration of the aqueous sodium hydroxide is about 10N.

In certain embodiments, following the addition of the aqueous sodium hydroxide the temperature of the resulting solution is warmed to room temperature.

In certain embodiments, the present methods further comprise precipitating the detritylated oligomeric compounds in ethanol.

In certain embodiments, the present methods provide greater than about 50 mmol of the detritylated oligomeric compounds. In certain embodiments, the present methods provide greater than about 100 mmol of the detritylated oligomeric compounds. In certain embodiments, the present methods provide greater than about 300 mmol of the detritylated oligomeric compounds.

In certain embodiments, the time required for essentially all of the 5'-trityl groups to be removed is reduced compared to time required when using standard methods. In certain embodiments, the percent of depurination of the detritylated oligomeric compounds is reduced compared to the percent of depurination when using standard methods.

DETAILED DESCRIPTION OF THE INVENTION

Provided herein are methods of preparing oligomeric compounds wherein the final detritylation step is performed at lower temperature and higher acidity (lower pH) compared to standard methods. These improved detritylation methods are particularly amenable to automated large scale solid phase synthesis of oligomeric compounds using the phosphoramidite approach. In certain embodiments, the detritylation methods disclosed herein provide oligomeric compounds having a lower percentage of depurination relative to oligomeric compounds prepared using standard methods. In certain embodiments, the detritylation methods disclosed herein provide oligomeric compounds having increased purity relative to oligomeric compounds prepared using standard methods. In certain embodiments, the final detritylation step is completed in less time using the detritylation methods provided herein compared to standard methods. In certain embodiments, the detritylation methods disclosed herein provide oligomeric compounds having a lower percentage of depurination in less time compared to standard methods.

The synthesis of oligomeric compounds is generally performed using solid phase chemistries wherein oligomeric compounds are assembled in an iterative process. A first monomer subunit is coupled to a free hydroxyl group attached to a solid support via a series of chemical reactions. This series of chemical reactions is iteratively repeated for each additional monomer subunit until the desired oligomeric compound having a predetermined length and base sequence is synthesized.

The full length oligomeric compound still comprising a 5'-terminal protecting group is treated with reagents to deprotect the phosphorus groups and then treated with a strong base such as ammonium hydroxide to cleave the oligomeric compound from the solid support. When the 5'-terminal protecting group is a 4,4'-dimethoxytrityl (DMT) group the oligomeric compound is referred to as a DMT-on oligomeric compound.

In certain embodiments, the protecting group at the 5'-terminus is a 4,4'-dimethoxytrityl (DMT) group which is acid labile and base stable. In certain embodiments, the 5'-terminal DMT group is intentionally left on (DMT-on) after the oligomeric compound has been synthesized as it serves as a chromatographic handle during reverse-phase HPLC purification. Following the purification process, the DMT group is removed from the oligonucleotide via the solution-phase detritylation reaction as shown below.

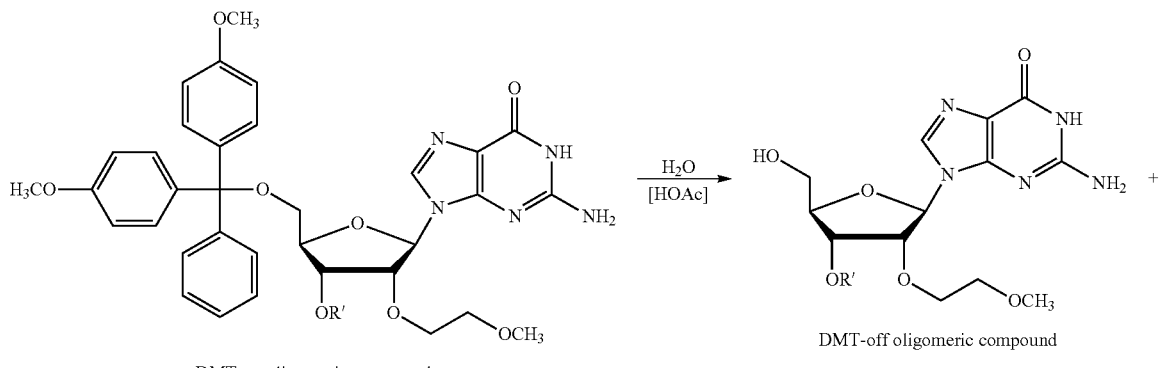

DMT-on oligomeric compound

DMT-off oligomeric compound

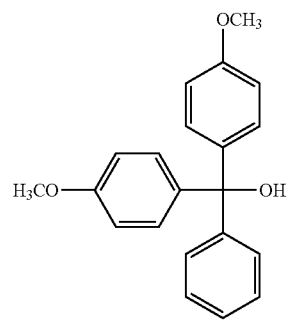

DMT alcohol

Wherein only the 5'-terminal monomer is shown and R' represents the remainder of the oligomeric compound. A 2'-MOE (2'-O—(CH$_2$)$_2$—OCH$_3$) substituted guanosine nucleoside is depicted as the monomer subunit at the 5'-terminus for illustration only. Any monomer subunit having a terminal hydroxyl group protected by a trityl group is amenable to the illustrated deprotection reaction. Acetic acid is shown in the reaction sequence but other acids will work to provide essentially the same results such as formic acid.

An undesired side reaction that occurs during the final detritylation step is depurination as illustrated below.

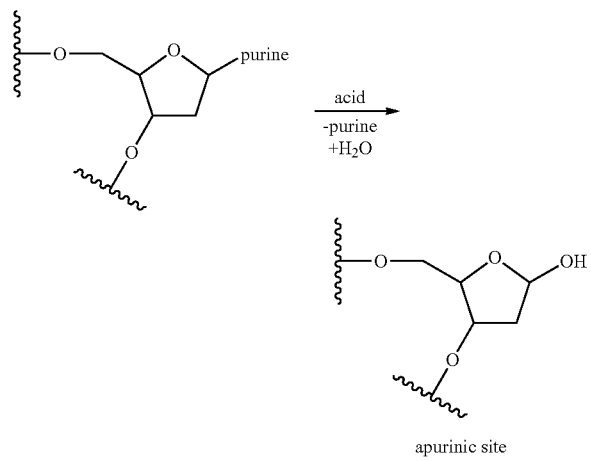

apurinic site

Based on historical data, when all other reaction variables are held constant (solution composition, temperature, reaction pH) the rate of detritylation varies based on the nucleotide on the 5'-terminus with the reaction rates taking on the order A>G>T>C. The rate of depurination depends on the number of deoxyadenosine and deoxyguanosine nucleosides in the specific oligomeric compound being detritylated. It is desired to maximize the degree of completion of the detritylation reaction while minimizing the amount of depurination, but compounds that detritylate slowly and have several deoxypurines are at the greatest risk of yielding unacceptably high levels of depurination when using standard methods for detritylation (see table 1, Example 3).

Following standard detritylation methods for certain oligomeric compounds have failed to provide acceptable levels of purity due at least to the percent of depurination in the final product (in excess of about 1.5% total depurination). In particular, oligomeric compounds having a 5'-terminal nucleobase (C<T<G<A) that slows down the detritylation reaction combined with a plurality of deoxypurine nucleosides may have a final purity that is unacceptable (see Table 1, Example 3).

Two oligomeric compounds were selected for further study in detritylation reactions under varied conditions (ISIS 420915, SEQ ID NO: 1 and ISIS 532401, Table 1, Example 3). Using standard methods to detritylate ISIS 532401 having a 5'-terminal cytosine nucleobase and six deoxypurines it was estimated, based on a reaction curve extrapolated out to completion, that after 4.5 days of reaction the product would contain 0.2% DMT-on and have an unacceptable 18% total depurination. Using standard methods for ISIS 420915 having a 5'-terminal thymine, two deoxyguanines and four deoxyadenines requires only about 5.5 hours to reach completion.

After running a series of experiments it was found that modifying the pH and temperature during the final detritylation step such that the reaction is performed at about 10° C. and at a pH of about 2.5 greatly decreased the rate of depurination and also increased the rate of detritylation for ISIS 532401. Using this modified method an improvement in the percent of depurination was also shown for ISIS 420915 (run at pH 3.0 and 10° C.). In certain embodiments, these modified conditions provided a benefit for non-problematic oligomeric compounds such as ISIS 420915 (SEQ ID NO: 1) that are routinely detritylated using standard methods. In certain embodiments, these modified conditions provide a method for detritylating oligomeric compounds that are problematic and are not amenable to detritylation using standard methods. Detritylation of ISIS 532401 using these modified conditions (pH 2.5, temperature 10° C.) on a manufacturing scale provided acceptable product with 0.03% DMT-on and 0.63% total depurination compared to expected 18% total depurination using standard methods.

The detritylation reactions have been performed at small and large scale with comparable results. For detritylation reactions on either a small scale (generally much smaller than about 100 mmol) or a large scale (from about 100 to about 600 mmol) the temperature of the solution throughout the detritylation and the quenching is maintained using a jacketed reaction vessel. Cooled coolant is cycled through the jacket to maintain the desired temperature for the solution within the vessel. For smaller scale runs cooling is provided using a Thermo Tek T255P recirculating chiller to control the temperature of the coolant (water) as it is circulated into the jacket. For larger scale runs cooling is provided using jacketed stainless steel tanks that are connected to a recycled chilled glycol system.

In certain embodiments, the solution is first cooled to about 10° C. and then the pH is adjusted to about 2.5 In certain embodiments, the temperature is maintained for the duration of the reaction. When the reaction is quenched with the aqueous sodium hydroxide solution, heat is released from the acid-base interaction. In certain embodiments, the temperature is maintained by adjusting the flow of coolant through the jacket. In certain embodiments, the temperature is maintained by adjustment of the rate of addition of the aqueous sodium hydroxide solution. In certain embodiments, the temperature is maintained by adjusting the flow of coolant through the jacket while simultaneously adjusting the rate of addition of the aqueous sodium hydroxide solution. In certain embodiments, the temperature of the solution while adding the aqueous sodium hydroxide solution is maintained at about 10° C. In certain embodiments, the temperature of the solution while adding the aqueous sodium hydroxide solution is maintained at about below about 25° C. In certain embodiments, the temperature of the solution while adding the aqueous sodium hydroxide solution is maintained at about below 35° C.

While not wanting to be bound by theory it is believed that the choice of acid used during the final detritylation step is not limited to glacial acetic acid. It was also expected that the detritylation reaction could be performed using a stronger acid with no negative effect on the reaction rate. Standard methods for detritylation generally use glacial acetic acid which is practical when targeting a pH of approximately 3.5. However, for lower pH values, larger quantities of this weak acid are required. For example, typical DMT-on reconstituted oligomeric compound solutions require the addition of approximately 5-10% v/v glacial acetic acid to reach pH 3.5 but require approximately 50% v/v glacial acetic acid to reach pH 2.5. To reduce the volume of acid required for larger scale oligomer synthesis a final detritylation reaction was performed using formic acid (pKa=3.77) instead of the standard acid Glacial acetic acid (pKa=4.76). The results of the detritylation reaction performed at 10° C. with the pH maintained at 2.5 using formic acid indicate that there is no major difference in detritylation rate or relative depurination rate.

In certain embodiments, the present detritylation methods are performed using standard reagents as illustrated in the standard methods illustrated in the examples. In certain embodiments, the present detritylation methods are performed at a temperature of from about 5° C. to about 15° C. In certain embodiments, the present detritylation methods are performed at about 10° C. In certain embodiments, the present detritylation methods are performed at a pH of from about 2.0 to about 3.5. In certain embodiments, the present detritylation methods are performed at a pH of from about 2.0 to about 3.0. In certain embodiments, the present detritylation methods are performed at a pH of about 2.5. In certain embodiments, the present detritylation methods are performed at a pH of about 2.5 and at a temperature of about 10° C. In certain embodiments, the selected temperature is maintained throughout the detritylation process from the addition of the acid until the reaction is fully quenched. In certain embodiments, the temperature is maintained at about 10° C. throughout the detritylation process from the addition of the acid until the reaction is fully quenched. In certain embodiments, the selected pH is maintained throughout the detritylation step. In certain embodiments, the pH is maintained at about 2.5 throughout the detritylation step.

The present detritylation methods are applicable to the preparation of oligomeric compounds comprising a wide range of monomer subunits such as nucleosides and modified nucleosides. In general, for the synthesis of oligomeric compounds each of the monomer subunits comprises a protected hydroxyl group and a phosphoramidite group. In certain embodiments, the hydroxyl protecting group is selected from substituted or unsubstituted trityl groups. In certain embodiments, the hydroxyl protecting group is 4,4'-dimethoxytrityl (DMT). In certain embodiments, the phosphoramidite group has the formula —P(NR$_2$R$_3$)(OR$_4$), wherein R$_2$ and R$_3$ are each, independently, C$_1$-C$_6$ straight or branched alkyl, which includes but is not limited to, methyl, ethyl, n-propyl, 2-propyl, n-butyl, iso-butyl, and similar alkyl groups, and R$_4$ is any group that is compatible with oligonucleotide synthesis that may be removed after synthesis is complete. Preferably, R$_4$ is a substituted C$_1$-C$_6$ alkyl including at least one heteroatom. Most preferably, R$_4$ is —CH$_2$CH$_2$CN. A preferred phosphoramidite group is diisopropylcyanoethoxy phosphoramidite (—P(N(CH(CH$_3$)$_2$)$_2$)(O(CH$_2$)$_2$CN)). In certain embodiments, the hydroxyl protecting group is 4,4'-dimethoxytrityl (DMT) and the phosphoramidite group is diisopropylcyanoethoxy phosphoramidite (—P(N(CH(CH$_3$)$_2$)$_2$)(O(CH$_2$)$_2$CN)).

In certain embodiments, methods of synthesizing of oligomeric compounds are provided that utilize support medium. In certain embodiments, reactive groups on the support medium are first functionalized with Unylinker™ linking groups prior to addition of the first monomer subunit. A first monomer subunit is attached to a support medium with subsequent monomer subunits iteratively coupled to provide a desired oligomeric compound. The industry standard for large scale oligomeric compound synthesis uses solid support media in a reaction vessel. The growing oligomeric compound is reacted and washed with various reagents and solvents while attached to the solid support. In certain embodiments, support media can be selected having variable solubility in different solvents to allow the growing support bound oligomeric compound to be either in or out of solution at various points in the synthesis process as desired. In certain embodiments, soluble supports include soluble polymer supports that allow precipitating and dissolving the iteratively synthesized product at desired points in the synthesis (Gravert et al., Chem. Rev., 1997, 97, 489-510).

The term "support media" is intended to include all forms of support, including those known to the art skilled for the synthesis of oligomeric compounds. Some representative support media that are amenable to the methods of the present invention include but are not limited to the following: crosslinked polystyrene (Primer Support 5G or Nitto-PhaseHL), controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225-231).

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "aralkyl" and "arylalkyl," refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "heteroarylalkyl," refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethylene, pyrimidinylethylene, napthyridinylpropylene and the like. Heteroarylalkyl groups as used herein may optionally include further substituent groups on one or both of the heteroaryl or alkyl portions.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "hydrocarbyl" includes radical groups that comprise C, O and H. Included are straight, branched and cyclic groups having any degree of saturation.

Such hydrocarbyl groups can include one or more additional heteroatoms selected from N and S and can be further mono or poly substituted with one or more substituent groups.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, hetero aromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein the terms "halo" and "halogen," refer to an atom selected from fluorine, chlorine, bromine and iodine.

As used herein the term "oxo" refers to the group (=O).

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

The terms "substituent" and "substituent group," as used herein, are meant to include groups that are typically added to a parent compounds or to further substituted substituent groups to enhance one or more desired properties or provide other desired effects. Substituent groups can be protected or unprotected and can be added to one available site or many available sites on a parent compound. As an example if a benzene is substituted with a substituted alky it will not have any overlap with a benzene that is substituted with substituted hydroxyl. In such an example the alkyl portion of the substituted alkyl is covalently linked by one of its carbon atoms to one of the benzene carbon atoms. If the alky is $C_1$ and it is substituted with a hydroxyl substituent group (substituted alkyl) then the resultant compound is benzyl alcohol ($C_6H_5CH_2OH$). If the benzene were substituted with a substituted hydroxyl group and the hydroxyl was substituted with a $C_1$ alkyl group then the resultant compound would be anisole ($C_6H_5OCH_3$).

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, hetero aryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein the term "nucleobase" generally refers to the nucleobase of a nucleoside or modified nucleoside. The term "heterocyclic base moiety" is broader than the term nucleobase in that it includes any heterocyclic base that can be attached to a sugar or sugar surrogate group to prepare a nucleoside or modified nucleoside. In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. Such heterocyclic base moieties include but are not limited to naturally occurring nucleobases (adenine, guanine, thymine, cytosine and uracil) and protected forms of unmodified nucleobases (4-N-benzoylcytosine, 6-N-benzoyladenine and 2-N-isobutyrylguanine) as well as modified (5-methyl cytosine) or non-naturally occurring heterocyclic base moieties and synthetic mimetics thereof (such as for example phenoxazines). In certain embodiments, each heterocyclic base moiety is, independently, uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine. In certain embodiments, each heterocyclic base moiety is, independently, uracil, thymine, cytosine, 5-methylcytosine, adenine, 6-N-benzoyladenine or guanine.

As used herein the term "sugar moiety" refers to naturally occurring sugars having a furanose ring system (ribose and 2'-deoxyribose), synthetic and/or non-naturally occurring sugars having a modified furanose ring system and sugar surrogates wherein the furanose ring has been replaced with a mono or polycyclic ring system such as for example a morpholino or hexitol ring system or a non-cyclic sugar surrogate such as that used in peptide nucleic acids. The sugar moiety of a monomer subunit provides the reactive groups that enable the linking of adjacent monomer subunits into an oligomeric compound. Illustrative examples of sugar moieties useful in the preparation of oligomeric compounds include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose wherein the ring oxygen atom has been replaced with a sulfur atom), bicyclic modified sugars (such as the 2'-O—CH($CH_3$)-4', 2'-O—$CH_2$-4' or 2'-O—($CH_2$)$_2$-4' bridged ribose derived bicyclic sugars) and sugar surrogates (such as for example when the ribose ring has been replaced with a morpholino, a hexitol ring system or an open non-cyclic system).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system such as that used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

As used herein the term "sugar substituent group" refers to a group that is covalently attached to a sugar moiety. In certain embodiments, examples of sugar substituent groups include without limitation halogen, alkyl, substituted alkyl, alkoxy, substituted alkoxy, alkenyl, substituted alkenyl, alkynyl, substituted alkynyl, amino, substituted amino, thio, substituted thio and azido. In certain embodiments the alkyl and alkoxy groups are $C_1$ to $C_6$. In certain embodiments, the alkenyl and alkynyl groups are $C_2$ to $C_6$. In certain embodiments, examples of sugar substituent groups include without limitation 2'-F, 2'-allyl, 2'-amino, 2'-azido, 2'-thio, 2'-O-allyl, 2'-OCF$_3$, 2'-O—$C_1$-$C_{10}$ alkyl, 2'-OCH$_3$, 2'-O(CH$_2$)—CH$_3$, 2'-OCH$_2$CH$_3$, 2'-O—(CH$_2$)$_2$CH$_3$, 2'-O—(CH$_2$)$_2$—O—CH$_3$ (MOE), 2'-O[(CH$_2$)$_n$O]$_m$CH$_3$, 2'-O(CH$_2$)$_2$SCH$_3$, 2'-O—(CH$_2$)$_3$—N(R$_p$)(R$_q$), 2'-O(CH$_2$)$_n$NH$_2$, 2'-O—(CH$_2$)$_2$—O—N(R$_p$)(R$_q$), O(CH$_2$)ON[(CH$_2$)$_n$CH$_3$]$_2$, 2'-O(CH$_2$)$_n$ONH$_2$, 2'-O—(CH$_2$)$_2$—O—(CH$_2$)$_2$—N(R$_p$)(R$_q$), 2'-O—CH$_2$C(=O)—N(R$_p$)(R$_q$), 2'-OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$)[N(R$_p$)(R$_q$)], wherein each R$_p$, R$_q$ and $R_r$ is, independently, H, substituted or unsubstituted $C_1$-$C_{10}$ alkyl or a protecting group and where n and m are from 1 to about 10.

In certain embodiments, examples of sugar substituent groups include without limitation 2'-F, 2'-allyl, 2'-amino, 2'-azido, 2'-thio, 2'-O-allyl, 2'-OCF$_3$, 2'-O—$C_1$-$C_{10}$ alkyl, 2'-O—CH$_3$, OCF$_3$, 2'- O—CH$_2$CH$_3$, 2'-O—(CH$_2$)$_2$CH$_3$, 2'-O—(CH$_2$)$_2$—O—CH$_3$ (MOE), 2'-O(CH$_2$)$_2$SCH$_3$, 2'-O—CH$_2$—CH=CH$_2$, 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(=O)—N(R$_m$)(R$_n$), 2'-O—CH$_2$C(=O)—N(H)—(CH$_2$)$_2$—N(R$_m$)(R$_n$) and 2'-O—CH$_2$—N(H)—C(=NR$_m$)[N(R$_m$)(R$_n$)] wherein each R$_m$ and R$_n$ is, independently, H, substituted or unsubstituted C$_1$-C$_{10}$ alkyl or a protecting group. In certain embodiments, examples of 2, -sugar substituent groups include without limitation fluoro, —O—CH$_3$, —O—CH$_2$CH$_3$, —O—(CH$_2$)$_2$CH$_3$, —O—(CH$_2$)$_2$—O—CH$_3$, —O—CH$_2$—CH=CH$_2$, —O—(CH$_2$)$_3$—N(R$_1$)(R$_2$), O—(CH$_2$)$_2$—O—N(R$_1$)(R$_2$), —O—(CH$_2$)$_2$—O—(CH$_2$)$_2$—N(R$_1$)(R$_2$), —O—CH$_2$C(=O)—N(R$_1$)(R$_2$), —O—CH$_2$C(=O)—N(H)—(CH$_2$)$_2$—N(R$_1$)(R$_2$) and —O—CH$_2$—N(H)—C(=NR$_1$)[N(R$_1$)(R$_2$)] wherein R$_1$ and R$_2$ are each independently, H or C$_1$-C$_2$ alkyl. In certain embodiments, examples of sugar substituent groups include without limitation fluoro, —O—CH$_3$, —O—(CH$_2$)$_2$—O—CH$_3$, —O—CH$_2$C(=O)—N(H)(CH$_3$), —O—CH$_2$C(=O)—N(H)—(CH$_2$)$_2$—N(CH$_3$)$_2$ and —O—CH$_2$—N(H)—C(=NCH$_3$)[N(CH$_3$)$_2$]. In certain embodiments, examples of sugar substituent groups include without limitation fluoro, —O—CH$_3$, —O—(CH$_2$)$_2$—O—CH$_3$, —O—CH$_2$C(=O)—N(H)(CH$_3$) and —O—CH$_2$C(=O)—N(H)—(CH$_2$)$_2$—N(CH$_3$)$_2$. Further examples of modified sugar moieties include without limitation bicyclic sugars (e.g. bicyclic nucleic acids or bicyclic nucleosides discussed below).

In certain embodiments, examples of "sugar substituent group" or more generally "substituent group" include without limitation one or two 5'-sugar substituent groups independently selected from C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl and halogen. In certain embodiments, examples of sugar substituent groups include without limitation one or two 5'-sugar substituent groups independently selected from vinyl, 5'-methyl, 5'-(S)-methyl and 5'-(R)-methyl. In certain embodiments, examples of sugar substituent groups include without limitation one 5'-sugar substituent group selected from vinyl, 5'-(S)-methyl and 5'-(R)-methyl.

In certain embodiments, examples of sugar substituent groups include without limitation substituted silyl, an RNA cleaving group, a reporter group, an intercalator, a group for improving pharmacokinetic properties, or a group for improving the pharmacodynamic properties of an oligomeric compound, and other substituents having similar properties. In certain embodiments, oligomeric compounds include modified nucleosides comprising 2'-MOE substituent groups (Baker et al., J. Biol. Chem., 1997, 272, 11944-12000). Such 2'-MOE substitution has been described as having improved binding affinity compared to unmodified nucleosides and to other modified nucleosides, such as 2'-O-methyl, 2'-O-propyl, and 2'-O-aminopropyl. Oligonucleotides having the 2'-MOE substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

Sugar moieties can be substituted with more than one sugar substituent group including without limitation 2'-F-5'-methyl substituted nucleosides (see PCT International Application WO 2008/101157, published on Aug. 21, 2008 for other disclosed 5',2'-bis substituted nucleosides). Other combinations are also possible, including without limitation, replacement of the ribosyl ring oxygen atom with S and further substitution at the 2'-position (see published U.S. Patent Application US2005-0130923, published on Jun. 16, 2005) and 5'-substitution of a bicyclic nucleoside (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the term "monomer subunit" is meant to include all manner of monomers that are amenable to oligomer synthesis. In general a monomer subunit includes at least a sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribonucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides and nucleosides having sugar surrogates. As used herein, the term "nucleoside" refers to a nucleobase-sugar combination. The two most common classes of such nucleobases are purines and pyrimidines. The term nucleoside includes β-D-ribonucleosides and β-D-2'-deoxyribonucleosides.

As used herein, the term "nucleotide" refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose.

In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols.

Modified nucleosides include abasic nucleosides but in general a heterocyclic base moiety is included for hybridization to a complementary nucleic acid target.

In certain embodiments, modified nucleosides include a furanose ring system or a modified furanose ring system. Modified furanose ring systems include 4'-S analogs, one or more substitutions at any position such as for example the 2', 3', 4' and 5' positions and addition of bridges for form additional rings such as a 2'-O—CH(CH$_3$)-4' bridge. Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as 2'-O—CH(CH$_3$)-4', 2'-O—CH$_2$-4' or 2'-O—(CH$_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons atoms. In certain embodiments, bicyclic nucleosides have a bridge between the 4' and 2' carbon atoms. Examples of such 4' to 2' bridged bicyclic nucleosides, include but are not limited to one of formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-C—H (CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO2008/150729, published Dec. 11, 2008); 4'-CH$_2$—O—N(CH$_3$)-2' (see U.S. Pat. No. 7,96,345, issued on Apr. 13, 2010); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., J. Org. Chem., 2009, 74, 118-134); and 4'-CH$_2$—CH$_2$-2' and 4'-CH$_2$—C—(=CH$_2$)-2' (and analogs thereof see published International Application WO 2008/154401, published on Dec. 8, 2008). Further bicyclic nucleosides have been reported in published literature (see for example: Srivastava et al., J. Am. Chem. Soc., 2007, 129(26) 8362-8379; Frieden et al., Nucleic Acids Research, 2003, 21, 6365-6372; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A, 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,741,457; 7,696,345; 7,547,684; 7,399,845; 7,053,207; 7,034,133; 6,794,499; 6,770,748; 6,670,461; 6,525,191; 6,268,490; U.S. Patent Publication Nos.: US2008-0039618; U.S. Patent Application Ser. Nos. 61/099,844; 61/097,787; 61/086,231; 61/056,564; 61/026,998; 61/026,995; 60/989,574; International applications WO2009/006478; WO2008/154401; WO2008/150729; WO 2007/134181; WO 2005/021570; WO 2004/106356; WO 94/14226). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups (generally forming a 4 to 6 membered ring with the parent sugar moiety) independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiments, modified nucleosides include nucleosides having sugar surrogate groups that include without limitation, replacement of the ribosyl ring with a sugar surrogate such as a tetrahydropyranyl ring system (also referred to as hexitol) as illustrated below:

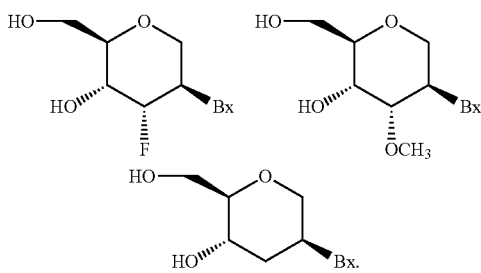

In certain embodiments, sugar surrogates are selected having the formula:

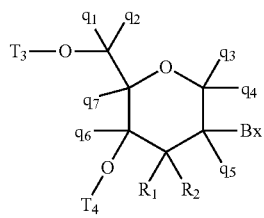

wherein:
Bx is a heterocyclic base moiety;
one of T$_3$ and T$_4$ is an internucleoside linking group attaching the tetrahydropyran nucleoside analog to the remainder of one of the 5' or 3' end of the oligomeric compound and the other of T$_3$ and T$_4$ is hydroxyl, a protected hydroxyl, a 5' or 3' terminal group or an internucleoside linking group attaching the tetrahydropyran nucleoside analog to the remainder of the other of the 5' or 3' end of the oligomeric compound;
q$_1$, q$_2$, q$_3$, q$_4$, q$_5$, q$_6$ and q$_7$ are each independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl; and
one of R$_1$ and R$_2$ is hydrogen and the other is selected from halogen, substituted or unsubstituted alkoxy, NJ$_1$J$_2$, SJ$_1$, N$_3$, OC(=X)J$_1$, OC(=X)NJ$_1$J$_2$, NJ$_3$C(=X)NJ$_1$J$_2$ and CN, wherein X is O, S or NJ$_1$ and each J$_1$, J$_2$ and J$_3$ is, independently, H or C$_1$-C$_6$ alkyl.

In certain embodiments, q$_1$, q$_2$, q$_3$, q$_4$, q$_5$, q$_6$ and q$_7$ are each H. In certain embodiments, at least one of q$_1$, q$_2$, q$_3$, q$_4$, q$_5$, q$_6$ and q$_7$ is other than H. In certain embodiments, at least one of q$_1$, q$_2$, q$_3$, q$_4$, q$_5$, q$_6$ and q$_7$ is methyl. In certain embodiments, THP nucleosides are provided wherein one of R$_1$ and R$_2$ is F. In certain embodiments, R$_1$ is fluoro and R$_2$ is H; R$_1$ is methoxy and R$_2$ is H, and R$_1$ is methoxyethoxy and R$_2$ is H.

Such sugar surrogates can be referred to as a "modified tetrahydropyran nucleoside" or "modified THP nucleoside". Modified THP nucleosides include, but are not limited to, what is referred to in the art as hexitol nucleic acid (HNA), altritol nucleic acid (ANA), and mannitol nucleic acid (MNA) (see Leumann, C. J., Bioorg. &Med. Chem., 2002, 10, 841-854).

In certain embodiments, oligomeric compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., J. Am. Chem. Soc., 2008, 130(6), 1979-1984; Horváth et al., Tetrahedron Letters, 2007, 48, 3621-3623; Nauwelaerts et al., J. Am. Chem. Soc., 2007, 129(30), 9340-9348; Gu et al. Nucleosides, Nucleotides & Nucleic Acids, 2005, 24(5-7), 993-998; Nauwelaerts et al., Nucleic Acids Research, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., J. Org. Chem., 2003, 68, 4499-4505; Verbeure et al., Nucleic Acids Research, 2001, 29(24), 4941-4947; Wang et al., J. Org. Chem., 2001, 66, 8478-82; Wang et al., Nucleosides, Nucleotides & Nucleic Acids, 2001, 20(4-7), 785-788; Wang et al., J. Am. Chem., 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

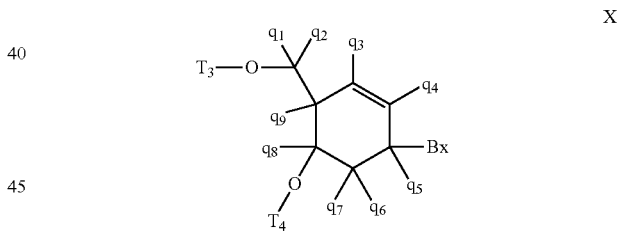

wherein independently for each of the at least one cyclohexenyl nucleoside analog of Formula X:
Bx is a heterocyclic base moiety;
one of T$_3$ and T$_4$ is an internucleoside linking group attaching the cyclohexenyl nucleoside to the remainder of one of the 5' or 3' end of the oligomeric compound and the other of T$_3$ and T$_4$ is hydroxyl, a protected hydroxyl, a 5' or 3' terminal group or an internucleoside linking group attaching the cyclohexenyl nucleoside to the remainder of the other of the 5' or 3' end of the oligomeric compound; and
q$_1$, q$_2$, q$_3$, q$_4$, q$_5$, q$_6$, q$_7$, q$_8$ and q$_9$ are each, independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. Bioorg. & Med.

*Chem.*, 2002, 10, 841-854). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

As used herein the term "reactive phosphorus" is meant to include groups that are covalently linked to a monomer subunit that can be further attached to an oligomeric compound that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH(CH$_3$)$_2$]$_2$]O(CH$_2$)$_2$CN) and H-phosphonate (—O*—P(=O)(H)OH), wherein the O* is normally attached to the 3'-position of the Markush group of Formula I. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Chiral auxiliaries are known in the art (see for example: Wang et al., *Tetrahedron Letters*, 1997, 38(5), 705-708; Jin et al., *J. Org. Chem*, 1997, 63, 3647-3654; Wang et al., *Tetrahedron Letters*, 1997, 38(22), 3797-3800; and U.S. Pat. No. 6,867,294, issued Mar. 15, 2005). Additional reactive phosphates and phosphites are disclosed in Tetrahedron Report Number 309 (Beaucage and Iyer, *Tetrahedron*, 1992, 48, 2223-2311).

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and CH$_2$ component parts.

As used herein, the term "oligomeric compound" refers to a contiguous sequence of linked monomer subunits. Each linked monomer subunit normally includes a heterocyclic base moiety but monomer subunits also include those without a heterocyclic base moiety such as abasic monomer subunits. In certain embodiments, at least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleosides having sugar surrogate groups.

In certain embodiments, oligomeric compounds comprise a plurality of monomer subunits independently selected from naturally occurring nucleosides, non-naturally occurring nucleosides, modified nucleosides and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-CH$_2$—C(=O)—N(H)-5'), amide-4 (3'-CH$_2$—N(H)—C(=O)-5') and methylphosphonate wherein a phosphorus atom is not always present. In certain embodiments, each internucleoside linkage is, independently, a phosphorothioate or a phosphodiester internucleoside linkage. In certain embodiments, essentially each internucleoside linkage is a phosphodiester internucleoside linkage. In certain embodiments, essentially each internucleoside linkage is, a phosphorothioate internucleoside linkage.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050;

5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are non-ionic. Neutral internucleoside linkages include without limitation, phosphotriesters, methylphosphonates, MMI (3'-$CH_2$—$N(CH_3)$—O-5'), amide-3 (3'-$CH_2$—C(=O)—N(H)-5), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

In certain embodiments, the steps for large scale synthesis of oligomeric compounds, other than coupling steps with bicyclic nucleosides of Formula I, are performed in accordance with published literature (see for example, Protocols for Oligonucleotides and Analogs, Agrawal, Ed., Humana Press, 1993, and/or RNA: Scaringe, *Methods*, 2001, 23, 206-217; Gait et al., *Applications of Chemically synthesized RNA in RNA:Protein Interactions*, Smith, Ed., 1998, 1-36; Gallo et al., *Tetrahedron*, 2001, 57, 5707-5713; Caruthers U.S. Pat. Nos. 4,415,732; 4,458,066; 4,500,707; 4,668,777; 4,973,679; and 5,132,418; and Koster U.S. Pat. Nos. 4,725, 677 and Re. 34,069).

Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl) oxy]methyl (2'-O—$CH_2$—O—$Si(iPr)_3$ (TOM) and the 5'-O-silyl ether-2'-ACE (5'-O-bis(trimethylsiloxy) cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1 (2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

All documents, or portions of documents, cited in this application, including, but not limited to, patents, patent applications, articles, books, and treatises, are hereby expressly incorporated by reference in their entirety for any purpose.

Those skilled in the art, having possession of the present disclosure will be able to prepare oligomeric compounds, comprising a contiguous sequence of linked monomer subunits, of essentially any viable length. While in certain embodiments, oligomeric compounds provided herein can be prepared as described, the following examples serve only to illustrate and are not intended to be limiting.

Example 1

Detritylation Using Standard Methods

Industry standard methods for synthesizing oligomeric compounds are well known in the art. Generally, reactive sites on a solid support material are coupled to monomers or universal linkers that provide protected reactive sites. The process of deblocking reactive sites and coupling monomers is performed iteratively to eventually provide an oligomeric compound having a predetermined length and base sequence. The phosphorus groups are deprotected and the oligomeric compound is cleaved from the solid support normally using a solution of ammonium hydroxide. After cleavage the 5'-protected oligomeric compound is purified and optionally precipitated one or more times. When the 5'-protecting group is a trityl group the oligomeric compound is referred to as a DMT-on oligomeric compound. The most commonly used 5'-protecting group is the 4,4'-dimethoxytrityl (DMT) group.

Standard protocols for performing the final detritylation of an oligomeric compound include dissolution of the DMT-on oligomeric compound in water, adjustment of the temperature to 22° C. and addition of acid to a pH of about 3.5. After the detritylation is complete the solution is quenched with base. In one such standard protocol (600 mmol support loading), the purified oligomeric compound is dissolved in purified water, the temperature is adjusted to 22° C. and the pH is adjusted to 3.5 by addition of glacial acetic acid. After detritylation is complete the reaction is quenched by addition of sodium hydroxide and the oligomeric compound is precipitated by addition of ethanol (generally the ethanol is in a stirred container and the quenched solution is added to it). The solution is decanted or pumped away from the precipitate and the precipitate is washed with ethanol to provide the detritylated oligomeric compound. For doing repeat runs on the same scale for the same oligomeric compound the detritylation time would be essentially the same for each successive run.

Example 2

Detritylation Using Standard Methods, Large Scale

DMT-on oligomeric compound is routinely prepared starting from an initial loading of the solid support of from about 200 to about 600 mmol. The DMT-on eluate (containing methanol and sodium acetate) from reverse phase HPLC purification is precipitated in ethanol to isolate the DMT-on oligomeric compound. After decanting the supernatant, the precipitated oligomeric compound is reconstituted with purified water to a targeted concentration. This typically yields a solution of 50 mg/g oligomeric compound, <1% w/w sodium acetate, and <10% w/w organic solvent (ethanol and methanol). This DMT-on reconstituted oligomeric compound solution is typically detritylated by first adjusting the pH of the mixing oligomeric compound to pH 3.5±0.2 with glacial acetic acid at 21-22° C. The reaction is allowed to proceed until the detritylation reaction is complete (essentially all of the trityl groups removed <0.2% DMT-on oligomeric compound relative to total oligomeric compound). The reaction time is generally based on laboratory pilot experiments or historical data. To stop the reaction, aqueous 10N sodium hydroxide is added to the solution to adjust the pH to 5.0-6.0. The solution is then immediately precipitated in ethanol to isolate the detritylated oligomeric compound.

Example 3

Nucleobase Influence on Detritylation Time

The nucleobases at the 5'-end of an oligomeric compound, in particular the 5'-terminal nucleobase, have a marked influence on the detritylation time. Following the standard detritylation protocols illustrated in examples 1 and 2, the detritylation times of various oligomeric compounds having either A, G, T or 5-methyl-C nucleobase located at the 5'-terminal nucleoside were compared. The detritylation time increases with the different 5'-terminal nucleobases in the order of A, G, T then 5-methyl-C. As shown in Table 1 below oligomeric compounds with a 5'-terminal 5-methyl-C nucleobase have markedly increased detritylation times. Detritylation times of oligomeric compounds having either A, G, T or 5-methyl-C as the 5'-terminal nucleobase are listed below in Table 1 below.

TABLE 1

| ISIS # | 5'-Nucleoside | Sequence (5' to 3') | Motif | Detritylation time (minutes) | Deoxy purines | % DMT on | SEQ ID NO |
|---|---|---|---|---|---|---|---|
| 304801 | A | $A_e G_e{}^m C_e T_e T_e (N_d)_{10} (N_e)_5$ | 5/10/5 | 66 | 3 | nd | 3 |
| 329993 | A | $A_e G_e{}^m C_e A_e T_e (N_d)_{10} (N_e)_5$ | 5/10/5 | 68 | 7 | nd | 4 |
| 404173 | A | $A_e A_e T_e G_e G_e (N_d)_{10} (N_e)_5$ | 5/10/5 | 93 | 2 | 0.01 | 5 |
| 404173 | A | $A_e C_e G_e G_e C_e (N_d)_{10} (N_e)_5$ | 5/10/5 | 123 | 5 | 0.11 | 6 |
| 505358 | G | $G_e{}^m C_e A_e G_e A_e (N_d)_{10} (N_e)_5$ | 5/10/5 | 112 | 8 | 0.05 | 7 |
| 449884 | G | $G_e G_e T_e (N_d)_{10} (N_e)_4$ | 3/10/4 | 155 | 5 | 0.03 | 8 |
| 426115 | G | $G_e{}^m C_e A_e G_e{}^m C_e (N_d)_{10} (N_e)_5$ | 5/10/5 | 108 | 5 | 0.54 | 9 |
| 440175 | G | $G_e G_e A_k (N_d)_{10} (N_k)_2 N_e$ | 3/10/3 | 210 | 3 | 0.06 | 10 |
| 463588 | G | $G_e{}^m C_e A_e{}^m C_e A_e (N_d)_{10} (N_e)_5$ | 5/10/5 | 376 | 6 | 0.05 | 11 |
| 494372 | T | $T_e G_e{}^m C_e T_e{}^m C_e (N_d)_{10} (N_e)_5$ | 5/10/5 | 134 | 4 | 0.06 | 12 |
| 416852 | T | $T_e G_e G_e T_e G_e (N_d)_{10} (N_e)_5$ | 5/10/5 | 189 | 3 | 0.03 | 13 |
| 546254 | T | $T_e G_e{}^m C_e A_e A_e (N_d)_{10} (N_e)_5$ | 5/10/5 | 278 | 3 | 0.03 | 14 |
| 183750 | T | $T_e G_e T_e C_e A_e (N_d)_{10} (N_e)_5$ | 5/10/5 | 331 | 4 | 0.01 | 15 |
| 396443 | T | $T_e{}^m C_e A_e (N_e)_{15}$ | (MOE)$_{18}$ | 404 | 0 | nd | 16 |
| 420915 | T | $T_e{}^m C_e T_e T_e G_e (N_d)_{10} (N_e)_5$ | 5/10/5 | 249 | 6 | 0.17 | 1 |

TABLE 1-continued

| ISIS # | 5'-Nucleoside | Sequence (5' to 3') | Motif | Detritylation time (minutes) | Deoxy purines | % DMT on | SEQ ID NO |
|---|---|---|---|---|---|---|---|
| 420476 | T | $T_e T_e{}^m C_e A_e T_e (N_d)_{10} (N_e)_5$ | 5/10/5 | 331 | 4 | 0.33 | 17 |
| 501861 | T | $T_e{}^m C_e A_e{}^m C_e A_e (N_d)_{10} (N_e)_5$ | 5/10/5 | 279 | 6 | 1.5 | 18 |
| 487660 | C | ${}^m C_e{}^m C_e A_e G_e{}^m C_e (N_d)_{10} (N_e)_5$ | 5/10/5 | 364 | 2 | 0.11 | 19 |
| 481464 | C | ${}^m C_k T_k A_k (N_d)_{10} (N_k)_3$ | 3/10/3 | 1176 | 4 | 0.02 | 20 |
| 405879 | C | ${}^m C_e{}^m C_e T_e G_e (N_d)_{10} (N_e)_5$ | 5/10/5 | 720 | 5 | 0.57 | 21 |
| 141923 | C | ${}^m C_e{}^m C_e T_e T_e{}^m C_e (N_d)_{10} (N_e)_5$ | 5/10/5 | 1500 | 5 | 1.02 | 22 |
| 532401 | C | ${}^m C_e{}^m C_e A_e{}^m C_e{}^m C_e (N_d)_{10} (N_e)_5$ | 5/10/5 | >>>1500 | 6 | nd | 23 |

Wherein C, A, T and G indicate the nucleobase for each nucleoside. N indicates a nucleoside with the nucleobase masked, subscript "d" indicates that the preceding nucleoside is a β-D-2'-deoxyribonucleoside, subscript "e" indicates that the preceding nucleoside is a 2'-O—(CH$_2$)$_2$—OCH$_3$ substituted nucleoside, subscript "k" indicates that the preceding nucleoside is a 6'-(S)—CH$_3$ bicyclic nucleoside (4'-C(H)((S)—CH$_3$)—O-2') and $^m$C indicates a 5-methyl cytosine. All internucleoside linkages are phosphorothioate.

Example 4

Modified Methods for Final Detritylation

An aqueous solution of a DMT-on oligomeric compound, such as one provided as per the procedures illustrated in examples 1 and 2, is cooled to from about 5-15° C. The cooled solution is then acidified by addition of glacial acetic acid to a pH of from 2 to 3.5. The pH is maintained while the solution is mixed. When the desired level of detritylation is achieved, the reaction is quenched by adding a solution of sodium hydroxide to achieve a pH in the range of 5.0-7.0. The temperature is maintained throughout the detritylation and quenching reactions. The resulting quenched solution is allowed to warm to ambient conditions with the pH maintained at from 5.0-7.0.

Example 5

Final Detritylation Using Modified Procedures with Formic Acid

ISIS 420915 (SEQ ID NO: 1) was detritylated using formic acid (pKa=3.77) substituted for the standard glacial acetic acid (pKa=4.76) to reduce the amount of acid required for the acidification step. The results of the detritylation reaction performed and maintained at 10° C. with the pH maintained at 2.5 using formic acid indicate that there is no major difference in detritylation rate or relative depurination rate relative an identical reaction sequence that used glacial acetic acid. The results suggest that the choice of acid does not impact the reaction rate as long as the same reaction pH is targeted.

| SEQ ID NO./ ISIS NO. | Composition (5' to 3') |
|---|---|
| 01/420915 | $T_e{}^{Me}C_e T_e T_e G_e GTTA{}^{Me}CATGAAA_e T_e{}^{Me}C_e{}^{Me}C_e{}^{Me}C_e$ |

Each nucleoside is linked to the next nucleoside by a phosphorothioate internucleoside linkage. Each nucleoside followed by a subscript "e" comprises a 2'-O(CH$_2$)$_2$—OCH$_3$ modified ribofuranose sugar moiety all other nucleosides comprise a 2'-deoxyribose sugar moiety. Each $^{Me}$C is a 5-methyl cytosine modified nucleoside.

In a subsequent experiment, ISIS 420915 (SEQ ID NO: 1) was detritylated using the standard conditions and the modified conditions to provide a direct comparison of the two methods using formic acid as opposed to the standard glacial acetic acid. A 50 mg/g solution of DMT-on ISIS 420915 was split into two equal volumes and one was detritylated using the standard conditions while the other was detritylated using the low temperature, low pH conditions (pH 2.5 and 10° C.). Both experiments used formic acid instead of glacial acetic acid. The experiments demonstrated that the low temperature, low pH conditions accelerated the detritylation rate while also decreasing the relative rate of depurination.

The data generated in this experiment demonstrated that the low temperature, low pH detritylation conditions afford a better depurination-to-detritylation profile compared to the standard conditions for ISIS 420915. The observed improvement (i.e. producing a smaller amount of depurination for a given amount of detritylation) was consistent with the data for ISIS 532401 and ISIS 443139. Additionally, this experiment illustrates that the observed improvement is not specific to glacial acetic acid.

Example 6

Final Detritylation Using Modified Procedures on Manufacturing Scale

Trityl eluate resulting from a 599 mmol large scale manufacturing run of ISIS 532401 (containing methanol and sodium acetate) from reverse phase HPLC purification was precipitated in ethanol to isolate the DMT-protected oligomeric compound. After decanting the supernatant, the precipitated oligomeric compound was reconstituted with purified water to a concentration of about 50 mg/g oligomeric compound, <1% w/w sodium acetate, and <10% w/w organic solvent (ethanol and methanol). The DMT-on reconstituted oligomeric compound solution was detritylated by first adjusting the pH to 2.47 (44.0 kg glacial acetic acid added to 56.1 kg of oligonucleotide solution) at about 10° C. The reaction was allowed to proceed for 209 minutes when the detritylation reaction was complete (<0.2% DMT-on oligomeric compound relative to total oligomeric compound). The pH was adjusted to 5.25 (58.9 kg of 10N aqueous sodium hydroxide) and the detritylated oligomeric compound was then precipitated by addition of the resulting basic solution to stirred ethanol. ISIS 532401 was obtained having only 0.03% DMT-on with 0.63% total depurination.

At both lab scale and manufacturing scale, the temperature of the detritylation and quenching reactions are controlled using a jacketed reaction vessel. By running a coolant through the jacket, the temperature of the reaction vessel and thus the solution inside the vessel is maintained at the desired temperature. At lower scale a ThermoTek T255P recirculating chiller is used to control the temperature of the coolant (water) as it is circulated into the jacket. At larger scale jacketed stainless steel tanks are used that are hooked up to the coolant (chilled glycol) system. The temperature is maintained by adjusting the flow and temperature of the coolant circulation in the jacketed reaction vessel.

In practice, the solution is first cooled to about 10° C. and then the pH is adjusted to about 2.5. The temperature is held at that temperature for the duration of this reaction. When the reaction is quenched with sodium hydroxide, heat is released from the acid-base interaction. The temperature is maintained by adjusting the rate at which the base is added. In practice it is desired to ensure that the temperature of the solution during base addition is maintained at less than 35° C.

Example 7

Final Detritylation Using Modified Procedures on Lab and Manufacturing Scale

Prior to manufacturing ISIS 443139 (SEQ ID NO:2) at large scale, a sample was generated in the laboratory for an initial assessment of the detritylation rate.

| SEQ ID NO./ ISIS NO. | Composition (5' to 3') |
|---|---|
| 02/443139 | $^{Me}C_{es}T_{eo}{}^{Me}C_{eo}A_{eo}G_{es}T_sA_sA_s{}^{Me}C_sA_sT_sT_s$ $G_sA_s{}^{Me}C_sA_{eo}{}^{Me}C_{eo}{}^{Me}C_{eo}A_{es}{}^{Me}C_e$ |

Each nucleoside followed by a subscript "s" is linked to the next nucleoside by a phosphorothioate internucleoside linkage and all other internucleoside linkages are phosphodiester. Each nucleoside followed by a subscript "e" comprises a 2'-O(CH$_2$)$_2$—OCH$_3$ modified ribofuranose sugar moiety all other nucleosides comprise a 2'-deoxyribose sugar moiety. Each $^{Me}C$ is a 5-methyl cytosine modified nucleoside.

A first sample of an aqueous solution of DMT-protected ISIS 443139 that was at approximately 50 mg/g oligonucleotide concentration was detritylated using standard conditions. Based on the data obtained in this initial experiment, it was determined that ISIS 443139 would require a reaction time of approximately 818 minutes to complete the reaction using the standard conditions. Using this data to extrapolate it was estimated that detritylation under these conditions would result in 2.7% Total Depurination, which is unacceptably high.

A second sample from the same aqueous solution of DMT-protected ISIS 443139 used above was detritylated using the modified low temperature and low pH conditions (acidified with glacial acetic acid to pH 2.5 at 10° C.). The results using the modified conditions showed a favorable decrease in the amount of depurination relative to detritylation. The results of this experiment demonstrated that the low temperature, low pH conditions required about 3.5 hours to complete the detritylation reaction (as opposed to 13.5 hours using the standard conditions). Additionally, the modified conditions resulted in about 1.0% Total Depurination as opposed to the 2.7% predicted for the standard conditions. These results were consistent with the previous data collected.

Having demonstrated that the low temperature, low pH detritylation conditions worked for ISIS 443139 at lab scale, the next step was to use the conditions at manufacturing scale for a 221-mmol batch. It was noted that for a 221-mmol batch, a solution of 50 mg/g oligonucleotide concentration would be too small of a working volume for the existing equipment train. Therefore, the solution was diluted with additional water down to an oligonucleotide concentration of 25 mg/g in order to achieve an appropriate working volume. Since oligonucleotide concentration is known to impact detritylation rate, another laboratory experiment was performed to measure the reaction kinetics of this less concentrated sample using low temperature, low pH conditions. The results showed that the lowering the oligonucleotide concentration increased the detritylation rate, which was expected. There was no significant difference in the depurination rates of the two concentrations at lab scale with respect to time.

The modified conditions were then applied to detritylate a 221-mmol manufacturing scale run using the procedures illustrated in Example 6. ISIS 443139 (~25 mg/g) was successfully detritylated at pH 2.52 and 10° C. for 293 minutes, resulting in 0.02% DMT-on and 1.2% Total Depurination.

Example 8

Effect of Temperature and pH on DMT-on Diastereomer Peaks on UV Chromatogram

During the detritylation of ISIS 532401 the reaction was monitored by Ion-Pair High Performance Liquid Chromatography with Ultraviolet detection coupled to Mass Spectrometry (IP-HPLC-UV-MS). The chromatograms of the oligonucleotide samples by IP-HPLC-UV-MS showed sets of peaks resolved. The earlier eluting peak resolves as a single peak and represents deprotected oligonucleotide where the DMT-group has been removed (DMT-off). The later eluting peaks represent the DMT-on oligonucleotide and partially resolve into two peaks. The two DMT-on peaks represent the two populations of diastereoisomers that differ only in the 5'-most internucleotide linkage (between the penultimate and last nucleotide). Typically, one population of diastereoisomers detritylates faster than the other, as evidenced by the disproportionate decrease in the peaks over the course of the reaction. In the case of detritylating ISIS 532401 under the standard conditions, one of the isomeric populations reacted extremely slowly. As the faster eluting peak disappears over time the later eluting peak is resistant to any but a slight reduction in height. However, the modified conditions combining low temperature and low pH (10° C. at pH 2.5) equalized the reaction rates of the two diastereomeric populations. The two peaks recede at essentially the same rate.

What is claimed is:

1. A method of detritylating 5'-trityl protected oligomeric compounds comprising:
   providing an aqueous solution of 5'-trityl protected oligomeric compounds;
   cooling the aqueous solution to from about 5° C. to about 15° C.;
   adjusting the pH of the cooled aqueous solution to from about 2.0 to about 3.5 by addition of an acid with mixing;
   mixing the acidified solution while maintaining the pH from about 2.0 to about 3.5 and maintaining the temperature at from about 5° C. to about 15° C. until essentially all of the 5'-trityl groups are removed; and
   adjusting the pH of the acidified solution to from about 5.0 to about 7.0 by addition of aqueous sodium hydroxide that is from about 1N to about 10N while maintaining the temperature below about 35° C. to provide the detritylated oligomeric compounds.

2. The method of claim 1 wherein each 5'-trityl group is 4,4'-dimethoxytrityl.

3. The method of claim 1 wherein the aqueous solution comprises from about 25 to about 150 mg of 5'-trityl protected oligomeric compounds per gram of water.

4. The method of claim 1 wherein the water used in any of the aqueous solutions is purified.

5. The method of claim 1 wherein the aqueous solution is cooled to from about 7° C. to about 13° C. until essentially all of the 5'-trityl groups are removed.

6. The method of claim 1 wherein the aqueous solution is cooled to about 10° C. until essentially all of the 5'-trityl groups are removed.

7. The method of claim 1 wherein the temperature of the aqueous solution is maintained at about 10° C. during the addition of aqueous sodium hydroxide.

8. The method of claim 1 wherein the temperature of the aqueous solution is maintained below 25° C. during the addition of aqueous sodium hydroxide.

9. The method of claim 1 wherein the pH of the cooled aqueous solution is adjusted to from about 2.0 to about 3.0.

10. The method of claim 1 wherein the pH of the cooled aqueous solution is adjusted to about 2.5.

11. The method of claim 1 wherein the acid is a weak acid.

12. The method of claim 11 wherein the weak acid is selected from glacial acetic acid, formic acid, citric acid, tartaric acid, malic acid, fumaric acid, lactic acid, ascorbic acid, benzoic acid oxalic acid and salicylic acid.

13. The method of claim 11 wherein the weak acid is a diluted strong acid selected from phosphoric acid, sulfuric acid and hydrochloric acid.

14. The method of claim 11 wherein the weak acid is an alkylated derivative of a strong acid selected from methanesulfonic acid, monochloroacetic acid, dichloroacetic acid and trifluoroacetic acid.

15. The method of claim 11 wherein the weak acid is glacial acetic acid.

16. The method of claim 11 wherein the weak acid is formic acid.

17. The method of claim 1 wherein the concentration of the aqueous sodium hydroxide is from about 7N to about 10N.

18. The method of claim 1 wherein the concentration of the aqueous sodium hydroxide is about 10N.

19. The method of claim 1 wherein following the addition of the aqueous sodium hydroxide the temperature of the resulting solution is warmed to room temperature.

20. The method of claim 1 further comprising precipitating the detritylated oligomeric compounds in ethanol.

21. The method of claim 1 providing greater than about 50 mmol of the detritylated oligomeric compounds.

22. The method of claim 1 providing greater than about 100 mmol of the detritylated oligomeric compounds.

23. The method of claim 1 providing greater than about 300 mmol of the detritylated oligomeric compounds.

24. The method of claim 1 wherein the time required for essentially all of the 5'-trityl groups to be removed is reduced compared to time required when using standard methods.

25. The method of claim 1 wherein the percent of depurination of the detritylated oligomeric compounds is reduced compared to the percent of depurination when using standard methods.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
tcttggttac atgaaatccc                                            20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
ctcagtaaca ttgacaccac                                            20

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 3
agcttnnnnn nnnnnnnnnn                                            20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 4
agcatnnnnn nnnnnnnnnn                                            20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 5
aatggnnnnn nnnnnnnnnn                                            20

<210> SEQ ID NO 6
<211> LENGTH: 20
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 6 acggcnnnn nnnnnnnnnn                                                   20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 7 gcagannnn nnnnnnnnnn                                                   20

<210> SEQ ID NO 8
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(17)
<223> OTHER INFORMATION: n is a, c, g, or t

<400> SEQUENCE: 8
ggtnnnnnnn nnnnnnn                                                     17

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 9 gcagcnnnn nnnnnnnnnn                                                   20

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(16)
<223> OTHER INFORMATION: n is a, c, g, or t

<400> SEQUENCE: 10
ggannnnnnn nnnnnn                                                      16

<210> SEQ ID NO 11
<211> LENGTH: 20
<212> TYPE: DNA
```

<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 11
gcacannnnn nnnnnnnnnn                                          20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 12
tgctcnnnnn nnnnnnnnnn                                          20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 13
tggtgnnnnn nnnnnnnnnn                                          20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 14
tgcaannnnn nnnnnnnnnn                                          20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 15
tgtcannnnn nnnnnnnnnn                                          20

<210> SEQ ID NO 16
<211> LENGTH: 18

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(18)
<223> OTHER INFORMATION: n is a, c, g, or t

<400> SEQUENCE: 16
tgannnnnnn nnnnnnnn                                              18

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 17
ttcatnnnnn nnnnnnnnnn                                            20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 18
tcacannnnn nnnnnnnnnn                                            20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 19
ccagcnnnnn nnnnnnnnnn                                            20

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(16)
<223> OTHER INFORMATION: n is a, c, g, or t

<400> SEQUENCE: 20
ctannnnnnn nnnnnn                                                16

<210> SEQ ID NO 21
```

```
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 21
ccttgnnnnn nnnnnnnnnn                                              20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(20)
<223> OTHER INFORMATION: n is a, c, g, or t

<400> SEQUENCE: 22
ccttcnnnnn nnnnnnnnnn                                              20
```